US010752961B2

(12) United States Patent
Tsuji et al.

(10) Patent No.: US 10,752,961 B2
(45) Date of Patent: Aug. 25, 2020

(54) METHOD FOR MEASURING EQUOL-PRODUCING ABILITY

(71) Applicant: KABUSHIKI KAISHA YAKULT HONSHA, Minato-ku (JP)

(72) Inventors: Hirokazu Tsuji, Funabashi (JP); Kaoru Moriyama, Saitama (JP); Koji Nomoto, Ota-ku (JP)

(73) Assignee: KABUSHIKI KAISHA YAKULT HONSHA, Minato-ku (JP)

( * ) Notice: Subject to any disclaimer, the term of this patent is extended or adjusted under 35 U.S.C. 154(b) by 24 days.

(21) Appl. No.: 15/768,755

(22) PCT Filed: Oct. 28, 2016

(86) PCT No.: PCT/JP2016/082128
§ 371 (c)(1),
(2) Date: Apr. 16, 2018

(87) PCT Pub. No.: WO2017/073753
PCT Pub. Date: May 4, 2017

(65) Prior Publication Data
US 2018/0312906 A1    Nov. 1, 2018

(30) Foreign Application Priority Data
Oct. 29, 2015 (JP) ................. 2015-212768

(51) Int. Cl.
*C12Q 1/689* (2018.01)
*C12Q 1/68* (2018.01)
*C12N 15/00* (2006.01)
*C12N 15/09* (2006.01)

(52) U.S. Cl.
CPC ........... *C12Q 1/689* (2013.01); *C12N 15/00* (2013.01); *C12N 15/09* (2013.01); *C12Q 1/68* (2013.01)

(58) Field of Classification Search
CPC .................... C12Q 1/68; C12Q 1/689
See application file for complete search history.

(56) References Cited

U.S. PATENT DOCUMENTS

| | | |
|---|---|---|
| 2010/0330627 A1 | 12/2010 | Shimada et al. |
| 2011/0318309 A1 | 12/2011 | Tsuji et al. |
| 2012/0064550 A1 | 3/2012 | Minekawa et al. |
| 2012/0190025 A1 | 7/2012 | Blackwood et al. |
| 2013/0071937 A1 | 3/2013 | Schmid |
| 2015/0240275 A1 | 8/2015 | Shimada et al. |
| 2016/0348155 A1 | 12/2016 | Guglielmetti et al. |

FOREIGN PATENT DOCUMENTS

| | | |
|---|---|---|
| JP | 2002-306175 A | 10/2002 |
| JP | 2010-169507 A | 8/2010 |
| JP | 2012-98034 A | 5/2012 |
| JP | 2013-500047 A | 1/2013 |
| JP | 2013-521479 A | 6/2013 |
| WO | WO 2010/098103 A1 | 9/2010 |
| WO | WO 2010/131660 A1 | 11/2010 |
| WO | WO 2011/017013 A2 | 2/2011 |
| WO | WO 2015/033304 A1 | 3/2015 |

OTHER PUBLICATIONS

Schroder, C. et al., Identification and Expression of Genes Involved in the Conversion of Daidzein and Genistein by the Equol-Forming Bacterium *Slackia isoflavoniconvertens*, Appl. Env. Microbiol., vol. 79, supplemental material, pp. 1-2 (Year: 2013).*
International Search Report dated Dec. 13, 2016, in PCT/JP2016/082128 filed Oct. 28, 2016.
Decroos, K. et al., "Isolation and characterization of an equol-producing mixed microbial culture from a human faecal sample and its activity under gastrointestinal conditions", Arch Microbiol, vol. 183, (2005), pp. 45-55.
Maruo, T. et al., "*Adlercreutzia equolifaciens* gen. nov., sp. nov., an equol-producing bacterium isolated from human faeces, and emended description of the genus *Eggerthella*", International Journal of Systematic and Evolutionery Microbiology, vol. 58, (2008), pp. 1221-1227.
Jin, J. et al., "*Slackia equolifaciens* sp. nov., a human intestinal bacterium capable of producing equol", International Journal of Systematic and Evolutionary Microbiology, vol. 60, (2010), pp. 1721-1724.
Extended European Search Report dated Feb. 4, 2019 in Patent Application No. 16859981.9, therein 9 pages.
Tsuji, H. et al. "Identification of an Enzyme System for Daidzein-to-Equol Conversion in *Slackia* sp. Strain NATTS" Applied and Environmental Microbiology, vol. 78, No. 4, XP055547524, 2012, pp. 1228-1236.
Rafii, F. "The Role of Colonic Bacteria in the Metabolism of the Natural Isoflavone Daidzin to Equol" Metabolites, vol. 5, No. 1, XP055547529, 2015, pp. 56-73.
Schröder, C. et al. "Identification and Expression of Genes Involved in the Conversion of Daidzein and Genistein by the Equol-Forming Bacterium *Slackia isoflavoniconvertens*" Applied and Environmental Microbiology, vol. 79, No. 11, XP055547535, 2013, pp. 3494-3502.
Tsuji, H. et al. "Isolation and characterization of the equol-producing bacterium *Slackia* sp. Strain NATTS" Archives of Microbiology, vol. 192, No. 4, XP055547542, 2010, pp. 279-287.

* cited by examiner

*Primary Examiner* — Teresa E Strzelecka
(74) *Attorney, Agent, or Firm* — Oblon, McClelland, Maier & Neustadt, L.L.P.

(57) ABSTRACT

Disclosed herein is a method for determining whether a test subject has equol-producing ability or not. The method involves measuring equol-producing ability of a test subject, wherein an equol converting enzyme gene derived from enteric bacteria of the test subject is detected using three types of primer sets described herein as the primer sets a) to c).

2 Claims, 3 Drawing Sheets
Specification includes a Sequence Listing.

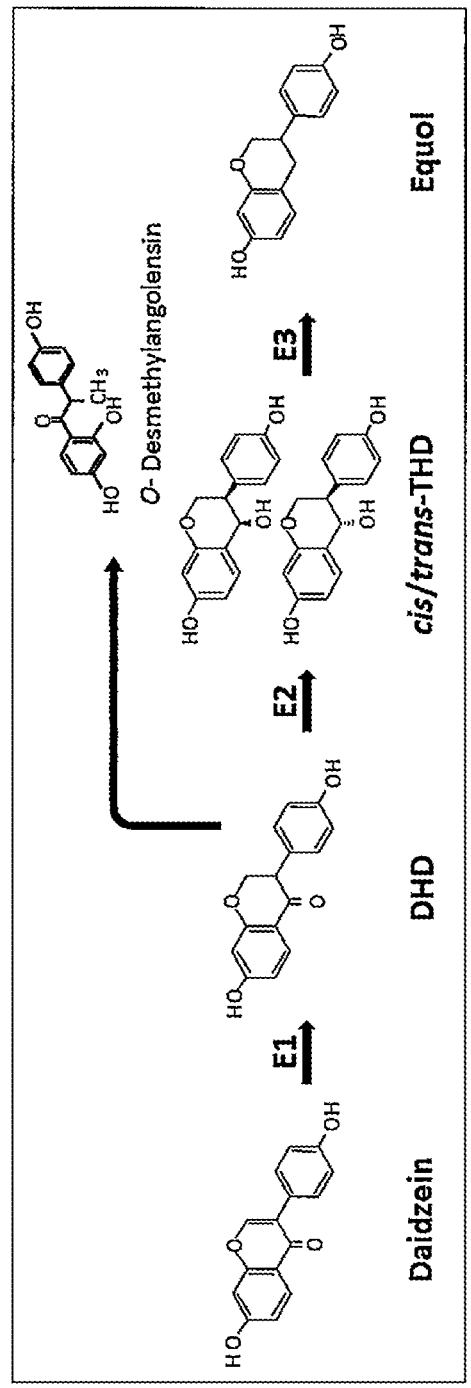
[Fig. 1]

[Fig. 2]
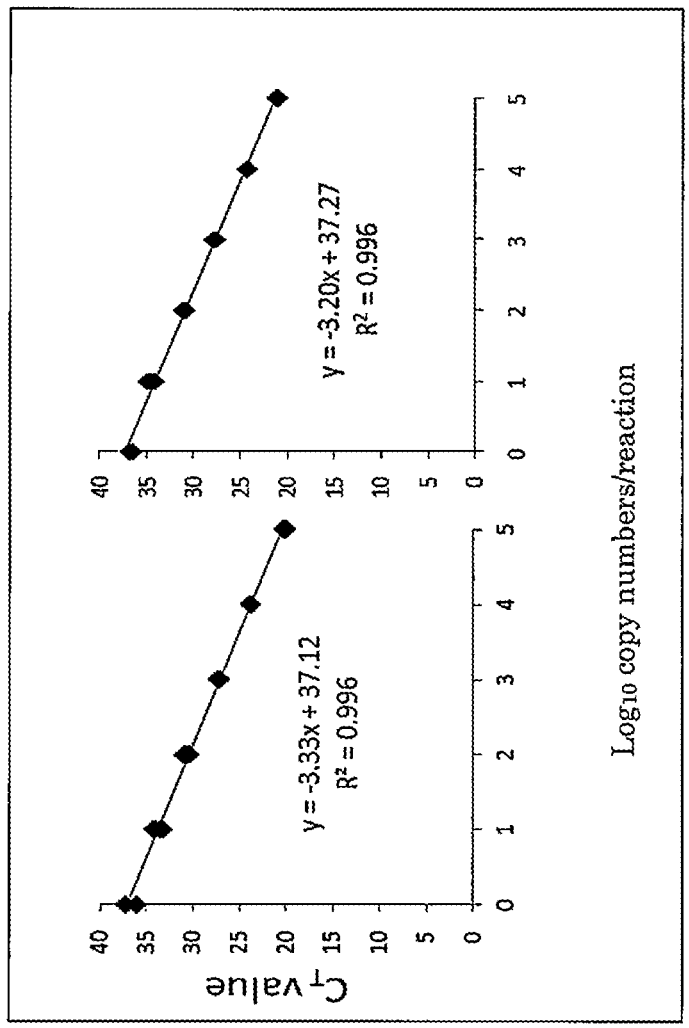

[Fig. 3]
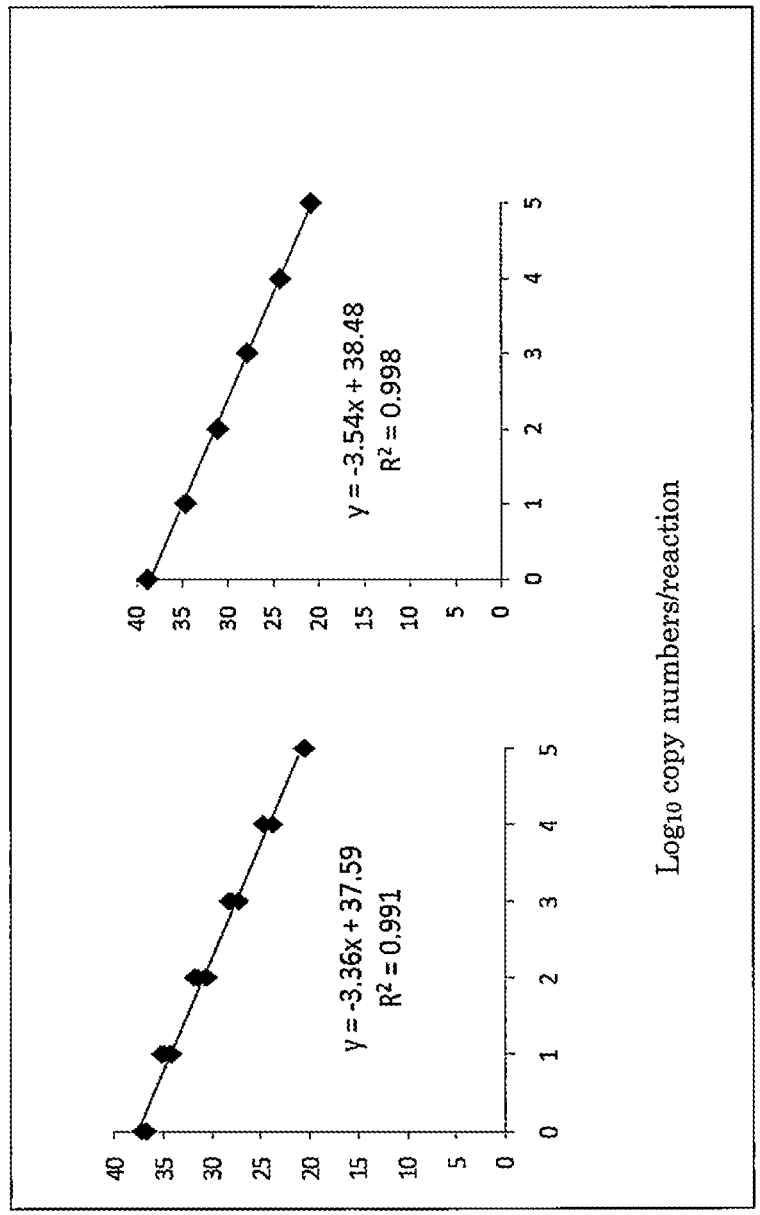

METHOD FOR MEASURING EQUOL-PRODUCING ABILITY

TECHNICAL FIELD

The present invention relates to a method for measuring equol-producing ability of a test subject.

BACKGROUND ART

Isoflavone, which is contained in a soy food in large amount, is known as a functional component having effects of relieving a climacteric disorder such as malaise, preventing osteoporosis, preventing hyperlipidemia and arteriosclerosis, and preventing breast cancer and prostate cancer. Recent studies clarified that daidzein, which is one of the isoflavone, is metabolized by internal enteric bacteria to equol having stronger estrogenic action and antioxidation effect (see FIG. 1). Accordingly, equol has been noted as a main active ingredient performing the above effects in the body.

It has been reported that production of equol from daidzein in the body does not equally occur among all human, the equol-producing ability varies among individuals, and 30 to 50% of human being has equol-producing ability. Thus, research for enteric bacteria having equol-producing ability (an equol-producing bacteria) has intensely been carried out, and *Bacteroides ovatus, Streptococcus intermedius, Streptococcus constellatus, Lactococcus garvieae, Slackia* spp. TM-30 strain, *Bifidobacterium adolescentis* TM-1 strain, *Bifidobacterium breve* JCM 1273, *Proprionobacterium freudenreichii, Bifidobacterium lactis, Lactobacillus acidophilus, Lactococcus lactis, Enterococcus faecium, Lactobacillus casei, Lactobacillus salivarius*, SNU-Julong732, gram positive bacterium do03, and *Slackia* sp. YIT 11861 (FERM BP-11231) have been reported as equol-producing bacteria (Patent Literature 1).

As described above, equol has various activities, and is expected to have preventive effects on sex hormone dependent diseases such as breast and prostate cancers. Thus, determining whether an individual has equol-producing ability or not is important.

Methods for determining whether a test subject has equol-producing ability or not include a method of detecting and measuring blood or urine equol metabolized from daidzein by an equol-producing bacteria in the present situation. A drawback to the method is that an amount of daidzein in blood or urine, and further an amount of equol vary depending on an amount of soybean intake before blood or urine collection. Specifically, when a test subject does not ingest soybean, equol is not detected in blood or urine. Thus, there is a risk that such a test subject can be misjudged to have no equol-producing ability whereas the test subject has an equol-producing bacteria.

On the other hand, a method for determining whether a test subject has equol-producing ability or not by presence or absence of an equol-producing bacteria may be possible. However, a method for precisely detecting the presence of all equol-producing bacteria has not been established, and such a method has not been reported.

CITATION LIST

Patent Literature

Patent Literature 1: WO 2010/098103 A

SUMMARY OF INVENTION

Technical Problem

The present invention relates to providing a method for measuring whether a test subject has equol-producing ability or not.

Solution to Problem

The present inventors, after pursuing studies in view of the above problems, have found that detection of a tetrahydrodaidzein (THD)-equol converting enzyme gene derived from enteric bacteria of a test subject using three specific types of primer sets can be used for a highly sensitive determination of whether the test subject has equol-producing ability or not.

The present invention relates to 1) to 7) below.

1) A method for measuring equol-producing ability of a test subject, wherein a THD-equol converting enzyme gene derived from enteric bacteria of the test subject is detected using three types of primer sets set forth in the following a) to c):

a) a primer pair comprising an oligonucleotide having a base sequence represented by SEQ ID NO: 1 and an oligonucleotide having a base sequence represented by SEQ ID NO: 2, or a primer pair comprising complementary sequences corresponding to said base sequences;

b) a primer pair comprising an oligonucleotide having a base sequence represented by SEQ ID NO: 3 and an oligonucleotide having a base sequence represented by SEQ ID NO: 4, or a primer pair comprising complementary sequences corresponding to said base sequences; and c) a primer pair comprising an oligonucleotide having a base sequence represented by SEQ ID NO: 5 and an oligonucleotide having a base sequence represented by SEQ ID NO: 6 or 7, or a primer pair comprising complementary sequences corresponding to said base sequences.

2) The method according to 1), wherein a THD-equol converting enzyme gene is detected using feces obtained from a test subject.

3) A primer pair comprising an oligonucleotide having a base sequence represented by SEQ ID NO: 1 and an oligonucleotide having a base sequence represented by SEQ ID NO: 2, or a primer pair comprising complementary sequences corresponding to said base sequences.

4) A primer pair comprising an oligonucleotide having a base sequence represented by SEQ ID NO: 3 and an oligonucleotide having a base sequence represented by SEQ ID NO: 4, or a primer pair comprising complementary sequences corresponding to said base sequences.

5) A primer pair comprising an oligonucleotide having a base sequence represented by SEQ ID NO: 5 and an oligonucleotide having a base sequence represented by SEQ ID NO: 6 or 7, or a primer pair comprising complementary sequences corresponding to said base sequences.

6) Three types of primer sets set forth in the following a) to c):

a) a primer pair comprising an oligonucleotide having a base sequence represented by SEQ ID NO: 1 and an oligonucleotide having a base sequence represented by SEQ ID NO: 2, or a primer pair comprising complementary sequences corresponding to said base sequences;

b) a primer pair comprising an oligonucleotide having a base sequence represented by SEQ ID NO: 3 and an oligonucleotide having a base sequence represented by SEQ ID NO: 4, or a primer pair comprising complementary sequences corresponding to said base sequences; and c) a primer pair comprising an oligonucleotide having a base sequence represented by SEQ ID NO: 5 and an oligonucleotide having a base sequence represented by SEQ ID NO: 6 or 7, or a primer pair comprising complementary sequences corresponding to said base sequences.

7) A kit for measuring equol-producing ability of a test subject, comprising three types of primer sets set forth in the following a) to c):

a) a primer pair comprising an oligonucleotide having a base sequence represented by SEQ ID NO: 1 and an oligonucleotide having a base sequence represented by SEQ ID NO: 2, or a primer pair comprising complementary sequences corresponding to said base sequences;

b) a primer pair comprising an oligonucleotide having a base sequence represented by SEQ ID NO: 3 and an oligonucleotide having a base sequence represented by SEQ ID NO: 4, or a primer pair comprising complementary sequences corresponding to said base sequences; and c) a primer pair comprising an oligonucleotide having a base sequence represented by SEQ ID NO: 5 and an oligonucleotide having a base sequence represented by SEQ ID NO: 6 or 7, or a primer pair comprising complementary sequences corresponding to said base sequences.

Effects of Invention

The method of the present invention can provide highly sensitive measurement of whether a test subject has an equol-producing bacteria or not, that is, equol-producing ability of the test subject regardless of ingestion of a daidzein-containing food such as soybean.

BRIEF DESCRIPTION OF DRAWINGS

FIG. 1 is a scheme showing an equol production pathway in daidzein metabolism.

FIG. 2 provides graphs (standard curves) showing quantitative properties of respective primers. Left: primers for detecting type A gene cluster (SL-F2/SL-R2), Right: primers for detecting type B gene cluster (Eght-F2/Egkm-R1)

FIG. 3 provides graphs (standard curves) showing quantitative properties of respective primers. Left: primers for detecting type C gene cluster-1 (Adht-F1/Adht-R1), Right: primers for detecting type C gene cluster-2 (Adht-F1/Adkm-R1)

DESCRIPTION OF EMBODIMENTS

According to a method for measuring equol-producing ability of a test subject of the present invention, a THD-equol converting enzyme gene derived from enteric bacteria of a test subject is detected using three types of primer sets set forth in the following a) to c). The detection includes qualitative and quantitative detection. The quantitative detection includes quantification of gene numbers (copy numbers) of THD-equol converting enzyme.

a) a primer pair comprising an oligonucleotide having a base sequence represented by SEQ ID NO: 1 and an oligonucleotide having a base sequence represented by SEQ ID NO: 2, or a primer pair comprising complementary sequences corresponding to said base sequences b) a primer pair comprising an oligonucleotide having a base sequence represented by SEQ ID NO: 3 and an oligonucleotide having a base sequence represented by SEQ ID NO: 4, or a primer pair comprising complementary sequences corresponding to said base sequences c) a primer pair comprising an oligonucleotide having a base sequence represented by SEQ ID NO: 5 and an oligonucleotide having a base sequence represented by SEQ ID NO: 6 or 7, or a primer pair comprising complementary sequences corresponding to said base sequences Any of the three types of primer sets set forth in a) to c) is a primer pair for amplifying a gene (hereinafter referred to as a "THD-equol converting enzyme gene") encoding equol converting enzyme E3 (hereinafter referred to as "THD-equol converting enzyme") concerning conversion from cis/trans-tetrahydrodaidzein (THD) to equol in daidzein metabolism (see FIG. 1).

THD-equol converting enzymes include some homologues, and thus THD-equol converting enzyme genes include some different sequences. The present inventors have found that the THD-equol converting enzyme genes can be classified into three types (i.e., gene clusters referring to type A gene cluster, type B gene cluster, and type C gene cluster as described below) on the basis of the difference in homology of base sequences. Homology between base sequences of genes within the same gene cluster is about 95 to 99%, and homology between base sequences of genes from different gene clusters is about 70 to 80%. Further, the present inventors have produced a primer set with respect to each of the gene types.

A primer set represented by a) is a primer pair which can amplify a THD-equol converting enzyme gene cluster (also referred to as "type A gene cluster") produced by, for example, *Slackia* sp. YIT 11861 strain, *Slackia isoflavoniconvertens* HE8 strain, and *Slackia* sp. MC6 strain. Specifically, the primer set comprises a first primer which is an oligonucleotide including a base sequence represented by SEQ ID NO: 1 (5'-CCCGCGCATTTGTGGAGAACT-3' (SL-F2)), and a second primer which is an oligonucleotide including a base sequence represented by SEQ ID NO: 2 (5'-CGTTCCGATATCGCCGAGGTTT-3' (SL-R2)).

A primer set represented by b) is a primer pair which can amplify a THD-equol converting enzyme gene cluster (also referred to as "type B gene cluster") produced by, for example, *Slackia equolifaciens* DZE strain, *Lactococcus garvieae* 20-92 strain, and *Eggerthella* sp. YY 7918 strain. Specifically, the primer set comprises a first primer which is an oligonucleotide including a base sequence represented by SEQ ID NO: 3 (5'-CGCTGCCTTCGAGTCCTCTA-3' (Eght-F2)), and a second primer which is an oligonucleotide including a base sequence represented by SEQ ID NO: 4 (5'-GGTGGAGGTGAAGATGTCG-3' (Egkm-R1)).

A primer pair represented by c) is a primer pair which can amplify a THD-equol converting enzyme gene cluster (also referred to as "type C gene cluster") produced by, for example, *Adlercreutzia equolifaciens* DSM 19450$^T$ strain and *Asaccarobactor celtus* DO-03 strain. Specifically, the primer pair comprises a first primer which is an oligonucleotide including a base sequence represented by SEQ ID NO: 5 (5'-CGTTCGATACTGAGTACGACCTG-3' (Adht-F1)), and a second primer which is an oligonucleotide including a base sequence represented by SEQ ID NO: 6 (5'-ATCCTTGAG GAAATCGATGGTA-3' (Adht-R1)) or a base sequence represented by SEQ ID NO: 7 (5'-AGTTTGCl-GATAGTGGCTGTA-3' (Adkm-R1)).

The first primer can be used as a forward primer for a nucleic acid amplification reaction such as PCR (polymerase chain reaction), and the second primer can be used as a reverse primer which is coupled with the first primer in the nucleic acid amplification reaction.

The primer set of the present invention includes a primer pair comprising complementary sequences corresponding to base sequences represented by SEQ ID NO: 1 and SEQ ID NO: 2 which can amplify type A gene cluster, a primer pair comprising complementary sequences corresponding to base sequences represented by SEQ ID NO: 3 and SEQ ID NO: 4 which can amplify type B gene cluster, and a primer pair comprising complementary sequences corresponding to base sequences represented by SEQ ID NO: 5 and SEQ ID NO: 6 or 7 which can amplify type C gene cluster.

In the present invention, oligonucleotides comprising a base sequence with 1 or 2 deletion, substitution, addition, or insertion in a base sequences represented by SEQ ID NOs: 1 to 7 and complementary sequences corresponding to said base sequences, or a base sequence having 90% or higher, or preferably 95% or higher identity to base sequences of SEQ ID NOs: 1 to 7 or complementary sequences corresponding to said base sequences, wherein said oligonucleotides respectively have equivalent functions to oligonucleotides comprising base sequences represented by SEQ ID NOs: 1 to 7 or complementary sequences corresponding to said base sequences as primers, are treated in the same way as oligonucleotides having base sequences represented by SEQ ID NOs: 1 to 7.

An oligonucleotide of the present invention can be synthesized by a publicly known method for synthesizing an oligonucleotide such as a phosphotriester method and a phosphodiester method using a generally-used automated DNA synthesizer (e.g., Model 394 DNA synthesizer manufactured by Applied Biosystems)

Detection of a THD-equol converting enzyme gene using the three types of primer sets set forth in a) to c) can be accomplished by a step of carrying out a nucleic acid amplification reaction using DNA extracted from a sample derived from a test subject as a template and using the above primer set, and a step of detecting an amplification product obtained by the nucleic acid amplification reaction.

The sample derived from a test subject for detecting a THD-equol converting enzyme gene includes a sample containing enteric bacteria of the test subject such as feces and contents of intestine. Feces are preferably used because they can easily be obtained.

DNA can be extracted from feces by a process similar to that in a conventional method for preparing genomic DNA. For example, DNA can be obtained from the whole or a part of samples derived from a test subject by any of a publicly known method, optionally, in combination with a pretreatment by extraction, separation, or purification as required. Specifically, DNA can be obtained by pretreating using a publicly known method such as filtration, centrifugation, or chromatography, and then extracting DNA using general-purpose methods such as "a physical crushing method including agitation in the presence of, for example, glass beads", "CTAB method", "a phenol chloroform method (PC method)", "a magnetic beads method", and "a silica column method", or using a combination of the general-purpose methods. In order to achieve a high detection sensitivity using PCR, it is preferred to obtain DNA in high concentrations. On the other hand, since a PCR inhibitory material coexists in a sample derived from a test subject such as a nucleic acid extract from feces, the inhibitory materials are preferably removed as much as possible to obtain DNA in high purity. For this purpose, it is specifically preferred to use FastDNA SPIN Kit for Feces (MP Biomedicals) which can extract DNA in high concentrations and high purity.

A nucleic acid amplification technique includes, but is not specifically limited to, a publicly known method utilizing a principle of a PCR method. Examples of the nucleic acid amplification technique include a PCR method, LAMP (Loop-mediated isothermal AMPlification) method, ICAN (Isothermal and Chimeric Primer-initiated Amplification of Nucleic acids) method, RCA (Rolling Circle Amplification) method, LCR (Ligase Chain Reaction) method, and SDA (Strand Displacement Amplification) method.

An amplification product of the nucleic acid amplification reaction can be detected by using a publicly known method for specifically recognizing the amplification product. For example, the obtained DNA can be electrophoresed to specifically detect a THD-equol converting enzyme gene as an electrophoretic band. The THD-equol converting enzyme gene can also be specifically detected by measuring absorbance. Further, a dNTP incorporated in the course of amplification reactions can be reacted with a labeling substance such as a radioisotope, a fluorescent substance, or a luminescent substance, and then the labeling substance can be detected. A method for observing the amplification product incorporated with the labeled dNTP can be any method publicly known in the art for detecting the above labeling substances. For example, when a radioisotope is used as a labeling substance, radioactivity can be measured using, for example, a liquid scintillation counter or a γ-counter. When fluorescent substance is used as a labeling substance, fluorescence can be detected using, for example, a fluorescent microscope or a fluorescence plate reader.

In the present invention, real-time PCR in which an amount of nucleic acids amplified in PCR is monitored and analyzed in real time is preferably used as a nucleic acid amplification technique because it provides rapid and quantitative analysis. Examples of the real-time PCR used include methods generally used in the art such as a TaqMan probe method, an intercalator method, and a cycling probe method.

Conditions for PCR are not specifically limited, and the optimum conditions can be established for each of PCR systems. Examples of the conditions for PCR include the following conditions:

1) Thermal denaturation of double-stranded DNA to provide single-stranded DNA: heating generally at about 93 to 95° C., and generally for about 10 seconds to 5 minutes;

2) Annealing: heating generally at about 50 to 60° C., and generally for about 10 seconds to 1 minutes; and 3) DNA elongation reaction: heating generally at about 70 to 74° C., and generally for about 30 seconds to 5 minutes.

The annealing and the DNA elongation reaction can be carried out concurrently instead of carrying out them separately.

A desired THD-equol converting enzyme gene can be amplified up to a detectable level by carrying out the above reactions 1) to 3) generally for about 30 to 50 cycles.

Such a series of PCR operations can be carried out using a commercially available PCR kit or PCR system according to its instructions. A real-time PCR can be carried out using a system specially designed for real-time PCR having a thermal cycler integrated with a spectrofluorometer such as ABI PRISM 7900 HT sequence detection system (Applied Biosystems).

In order to measure an amount of DNA, a sample containing serially diluted standard DNA solution with a known DNA concentration is subjected to PCR. Then a standard curve is generated by plotting the initial amount of DNA (along the horizontal axis) versus cycle numbers (threshold cycle: $C_T$ value) for achieving a certain amount of the PCR amplification product using the above DNA as a template (along the vertical axis). A sample with an unknown DNA concentration is also subjected to the PCR reaction under the same conditions to provide a $C_T$ value. The amount of the desired DNA in the sample can be obtained from the $C_T$ value of the sample and the standard curve.

Three types of primer sets set forth in a) to c) of the present invention can be provided as a kit for more convenient measurement of equol-producing ability of a test subject. Any kit can be used as a kit of the present invention so long as it includes the three types of primer sets set forth in a) to c). The kit of the present invention may include, as required, a reagent for PCR such as a reagent for DNA extraction, a buffer for PCR, or a DNA polymerase, a DNA solution containing a PCR amplification region which can be a positive control for the reaction, a reagent for detection such as a staining reagent or a gel for electrophoresis, and an instructions describing methods for using the kit. The reagent which may be included in the kit can be a solution or a lyophilized material.

Accordingly, comprehensive detection of THD-equol converting enzyme genes derived from enteric bacteria of a test subject can be accomplished by a method of the present invention. This may lead to highly successful determination of whether a test subject is an equol producer or not.

EXAMPLES

Example 1: Design of Primers Targeting THD-Equol Converting Enzyme Gene of Human Derived Equol-Producing Bacteria An equol production pathway in daidzein metabolism is shown in FIG. 1. Primers targeting each of the three types of equol converting enzyme genes were produced as primers capable of detecting an equol-producing bacteria.

(1) Materials
(a) Strains Used

Strains shown in Table 1 stored in Yakult Honsha Co., Ltd. CENTRAL INSTITUTE were used. Initial bacterial numbers of each bacterial strain were adjusted to about $1 \times 10^5$ cells.

Culture conditions of each strain are shown in Table 1. Details of culture conditions A to C are described below.

Condition A: Bacteria were cultured using Modified GAM Agar medium (Nissui) supplemented with 1% glucose at 37° C. for 24 hours under anaerobic conditions. Then, colonies on the agar culture medium were recovered using Modified GAM Broth (Nissui).

Condition B: Bacteria were cultured using Modified GAM Broth (Nissui) supplemented with 0.5% Glucose, 0.1% Cellobiose, 0.1% Maltose, and 0.1% Starch at 37° C. for 48 hours under anaerobic conditions.

Condition C: Bacteria were cultured using Willkins-Chalgren Anaerobe broth at 37° C. for 24 hours under anaerobic conditions.

Bacterial numbers in each of the bacterial suspensions were determined by DAPI method (J. Microbiol. Methods 37, 215-221), and culture broth of each bacteria was prepared on the basis of the bacterial numbers to achieve $10^9$ cells/ml. The obtained culture broths were used as pure bacterial culture broths of the respective strains.

TABLE 1

| Bacterial strain number | Bacterial species | Strain | Culture conditions |
|---|---|---|---|
| 1 | *Slackia* sp. | YIT 11861 | Condition A |
| 2 | *Slackia isoflavoniconvertens* | HE8 | Condition A |
| 3 | *Slackia* sp. | MC6 | Condition A |
| 4 | *Adlercreutzia equolifaciens* | DSM 19450$^T$ | Condition A |
| 5 | *Asaccarobactor celtus* | DO-03 | Condition A |
| 6 | *Enterorhabdus mucosicola* | DSM 19490$^T$ | Condition C |
| 7 | *Slackia equolifaciens* | DZE | Condition B |

(2) Methods

Before producing primers, a molecular phylogenetic analysis was carried out using Clustal X software on the basis of information on THD-equol converting enzyme genes contained in equol-producing bacteria shown in Table 2, and then three types of THD-equol converting enzyme genes were identified. The THD-equol converting enzyme genes were classified as type A gene cluster, type B gene cluster, and type C gene cluster, respectively (types of THD-equol converting enzyme genes of respective strains are shown in Table 2). MC6 strain in equol-producing bacteria shown in Table 1 is a novel bacteria isolated and identified by the present inventors.

In connection with sequences of THD-equol converting enzyme genes contained in 8 strains of equol-producing bacteria shown in Table 2, sequences of the genes belonging to each of the types were aligned using Clustal X software, and primers targeting each type of the genes were designed on the basis of the obtained specific sequence.

In attempts to design primers by aligning the sequences of the THD-equol converting enzyme genes contained in 8 strains shown in Table 2 as a whole without dividing them into types using Clustal X software, a specific sequence with high gene sequence homology could not be found out, and thus no primer was produced. Accordingly, discovery of the existence of the three types was found to be important to produce primers.

TABLE 2

| Bacterial strain number | Bacterial species | Strain | Types of THD-equol converting enzyme genes |
|---|---|---|---|
| 1 | *Slackia* sp. | YIT 11861 | Type A |
| 2 | *Slackia isoflavoniconvertens* | HE8 | Type A |
| 3 | *Slackia* sp. | MC6 | Type A |
| 4 | *Adlercreutzia equolifaciens* | DSM 19450$^T$ | Type C |
| 5 | *Asaccarobactor celtus* | DO-03 | Type C |
| 6 | *Enterorhabdus mucosicola* | DSM 19490$^T$ | Type C |
| 7 | *Slackia equolifaciens* | DZE | Type B |
| 8 | *Lactococcus garvieae* | 20-92 | Type B |
| 9 | *Eggerthella* sp. | YY 7918 | Type B |

(3) Results

Sequences of the designed primers are shown in Table 3. In primers targeting the type C gene cluster, primers targeting the type C gene cluster-1 were obtained by aligning sequences of THD-equol converting enzyme genes contained in bacterial strain numbers 4 and 5 in Table 2 using Clustal X software, and designing the primer on the basis of the obtained specific sequence. Primers targeting the type C gene cluster-2 were obtained by aligning sequences of THD-equol converting enzyme genes contained in bacterial strain numbers 4 to 6 in Table 2 using Clustal X software, and designing the primer on the basis of the obtained specific sequence.

TABLE 3

| Target THD-equol converting enzyme gene | Primer name | Sequence (5'-3') |
|---|---|---|
| Type A gene cluster | SL-F2 | CCCGCGCATTTGTGGAGAACT (SEQ ID NO: 1) |
|  | SL-R2 | CGTTCCGATATCGCCGAGGTTT (SEQ ID NO: 2) |
| Type B gene cluster | Eght-F2 | CGCTGCCTTCGAGTCCTCTA (SEQ ID NO: 3) |
|  | Egkm-R1 | GGTGGAGGTGAAGATGTCG (SEQ ID NO: 4) |
| Type C gene cluster-1 | Adht-F1 | CGTTCGATACTGAGTACGACCTG (SEQ ID NO: 5) |
|  | Adht-R1 | ATCCTTGAGGAAATCGATGGTA (SEQ ID NO: 6) |
| Type C gene cluster-2 | Adht-F1 | CGTTCGATACTGAGTACGACCTG (SEQ ID NO: 5) |
|  | Adkm-R1 | AGTTTGCGCGATAGTGGCTGTA (SEQ ID NO: 7) |

Test Example 1: Specificity of Primers Targeting THD-Equol Converting Enzyme Gene (1) Materials
(a) Strains Used In addition to strains shown in Table 1, strains shown in Table 4 stored in Yakult Honsha Co., Ltd. CENTRAL INSTITUTE were used. Initial bacterial numbers of each bacterial strain were adjusted to about $1 \times 10^5$ cells.

Culture conditions of each strain are shown in Table 4. Details of culture conditions A to F are described below.

Condition A: Bacteria were cultured using Modified GAM Broth (Nissui) supplemented with 1% glucose at 37° C. for 24 hours under anaerobic conditions.

Condition B: Bacteria were cultured using Modified GAM Broth Glucose (Nissui) supplemented with 0.5% glucose at 37° C. for 24 hours under anaerobic conditions.

Condition C: Bacteria were cultured using Modified GAM Broth (Nissui) at 37° C. for 24 hours under anaerobic conditions.

Condition D: Bacteria were cultured using Modified GAM Broth (Nissui) supplemented with 1.5% Na-Lactate at 37° C. for 24 hours under anaerobic conditions.

Condition E: Bacteria were cultured using Modified GAM Broth (Nissui) supplemented with 0.5% Glucose, 0.1% Cellobiose, 0.1% Maltose, and 0.1% Starch at 37° C. for 48 hours under anaerobic conditions.

Condition F: Bacteria were cultured using Modified GAM Agar medium (Nissui) supplemented with 1% glucose at 37° C. for 24 hours under anaerobic conditions. Then, colonies on the agar culture medium were recovered using Modified GAM Broth (Nissui).

Bacterial numbers in each of the bacterial suspensions were determined by DAPI method, and culture broth of each bacteria was prepared on the basis of the bacterial numbers to achieve $10^9$ cells/mL. The obtained culture broths were used as pure bacterial culture broths of the respective strains.

TABLE 4

| Bacterial strain number | Bacterial species | Strain | Culture conditions |
|---|---|---|---|
| 10 | Clostridium perfringens | JCM 1290$^T$ | Condition A |
| 11 | Clostridium ramosum | JCM 1298$^T$ | Condition A |
| 12 | Clostridium difficile | DSM 1296$^T$ | Condition A |
| 13 | Blautia prosucta | JCM 1471$^T$ | Condition B |
| 14 | Faecalibacteriium prausnitzii | ATCC 27768$^T$ | Condition A |
| 15 | Bacteroides vulgatus | ATCC 8482$^T$ | Condition C |
| 16 | Collinsella aerofaciens | DSM 3979$^T$ | Condition A |
| 17 | Bifidobacterium longum | ATCC 15707$^T$ | Condition B |
| 18 | Fusobacterium russii | ATCC 25533 | Condition A |
| 19 | Akkermansia muciniphila | ATCC BAA-835$^T$ | Condition A |
| 20 | Veillonella parvula | GIFU 7884$^T$ | Condition D |
| 21 | Acidaminococcus fermentans | GIFU 7844$^T$ | Condition C |
| 22 | Atopobium fosser | JCM 9981$^T$ | Condition E |
| 23 | Atopobium parvulum | JCM 10300$^T$ | Condition A |
| 24 | Atopobium minutum | JCM 1118$^T$ | Condition E |
| 25 | Atopobium rimae | JCM 10299$^T$ | Condition A |
| 26 | Atopobium vaginae | DSM 15829$^T$ | Condition E |
| 27 | Collinsella intestinalis | JCM 10643$^T$ | Condition A |
| 28 | Collinsella stercoris | JCM 10641$^T$ | Condition A |
| 29 | Cryptobacterium curtum | ATCC 700683$^T$ | Condition E |
| 30 | Denitrobacterium detoxificans | CCUG 56741$^T$ | Condition E |
| 31 | Eggerthella lenta | JCM 9979$^T$ | Condition F |
| 32 | Olsenella profusa | JCM 14553$^T$ | Condition E |
| 33 | Olsenella uli | JCM 12494$^T$ | Condition E |
| 34 | Paraeggerthella hongkongensis | JCM 14552$^T$ | Condition F |
| 35 | Slackia exigua | JCM 11022$^T$ | Condition F |
| 36 | Slackia faecicanis | JCM 14555$^T$ | Condition F |
| 37 | Slackia heliotrinireducens | JCM 14554$^T$ | Condition F |

(2) Methods

Specificity studies were performed on the most dominant enteric bacteria (No. 10 to 21), bacteria belonging to Coriobacteriaceae (No. 22 to 37), and human derived equol-producing bacteria (No. 1 to 7) shown in Table 1 and Table 4.

Specificity of primers was studied by extracting DNAs from the pure bacterial culture broth of each strain using a publicly known method (Appl. Environ. Microbiol. 70: 167-73), and then performing quantitative PCR.

A method for generating a standard curve used in quantitative PCR is provided below. *Slackia* sp. YIT 11861 strain was used for generating a standard curve of primers targeting type A gene cluster. Similarly, *Slackia equolifaciens* DZE was used for generating that of primers targeting type B gene cluster, and *Adlercreutzia equolifaciens* DSM 19450$^T$ was used for generating that of primers targeting type C gene clusters-1 and -2. PCR was performed with primers shown in Table 3 using DNA extracted from a pure bacterial culture broth of each strain as a template. The amplification products were purified using PCR Product Purification Kit (Roche), and absorbance (A. 280 nm) of the DNA was measured using Life Science UV/Vis Spectrophotometer DU730 (BECKMAN COULTER) to calculate a weight of DNA from the absorbance value. Copy numbers were calculated from weight of the DNA and an amount of molecules per 1 mole of the amplification product. The purified DNAs were diluted with TE buffer (pH 8.0) to achieve copy numbers of $2 \times 10^8$ copy numbers/mL.

A DNA solution with copy numbers of $2 \times 10^8$ copy numbers/mL was used as an undiluted solution and diluted by 10-fold serial dilution using TE buffer (pH 8.0). From the diluted solution, 5 μL of the diluted DNA solution was sampled to achieve $10^0$ to $10^5$ copy numbers per one reaction and subjected to quantitative PCR. Conditions for the quantitative PCR are provided below. Ampdirect plus (SHIMADZU) was used for the quantitative PCR. Composition of a reaction solution was 10 μL of Ampdirect plus, 0.08 μL of 300-fold diluted SYBR Green 1 (LONZA), 0.4 μL of ROX Reference Dye (Invitrogen), 0.08 μL of 50 μM Primer 1 and 0.08 μL of 50 μM Primer 2, 0.08 μL of rTaq (TaKaRa Bio.), 0.1 μL of Taq start antibody (Clontech), and 5 μL of the above diluted DNA solution. An amount of the reaction solution was then adjusted to 20 μL with NFW. PCR was performed under the following conditions: 45 cycles of 94° C. for 5 minutes, 94° C. for 20 seconds, 60° C. for 20 seconds, and 72° C. for 50 seconds. A standard curve was generated by plotting the $C_T$ value obtained by the quantitative PCR (along the vertical axis) versus the copy numbers per one reaction (along the horizontal axis).

The DNA extracted from each of the pure bacterial culture broths of strains shown in Table 1 and Table 4 was subjected to PCR in an amount of $10^6$ copy numbers per one PCR reaction. $C_T$ value was obtained using the DNA extracted from each of the pure bacterial culture broths of the strains as a template. Copy numbers were calculated from the $C_T$ value using the standard curve. Then, primers producing copy numbers of $10^5$ or more were judged as positive (+), $10^1$ or less were judged as negative (−), and $10^1$ to $10^5$ (more than $10^1$ and less than $10^5$) were judged as (±).

(3) Results

Results of specificities are shown in Table 5. Using primers for detecting type C gene cluster-1, no amplification of DNA of bacterial strain number 6 having type C gene was observed. However, using the other primers, amplifications of DNA of target type equol-producing bacteria were observed. With respect to any of the designed primers, no amplification of DNA of the most dominant enteric bacteria (No. 10 to 21), bacteria belonging to Coriobacteriaceae (No. 22 to 37), and equol-producing bacteria except for the target type bacteria was observed. Accordingly, it is found that each of the primers has a high specificity. It is also found that primers for detecting type C gene cluster-2 have higher specificity than primers for detecting type C gene cluster-1, and are preferred as primers for detecting type C gene cluster.

TABLE 5

| Bacterial strain number | Primers | | | |
|---|---|---|---|---|
| | For detecting type A gene cluster | For detecting type B gene cluster | For detecting type C gene cluster-1 | For detecting type C gene cluster-2 |
| 1 | + | − | − | − |
| 2 | + | − | − | − |
| 3 | + | − | − | − |
| 4 | − | − | + | + |
| 5 | − | − | + | + |
| 6 | − | − | − | + |
| 7 | − | + | − | − |
| 10 | − | − | − | − |
| 11 | − | − | − | − |
| 12 | − | − | − | − |
| 13 | − | − | − | − |

TABLE 5-continued

| Bacterial strain number | Primers | | | |
|---|---|---|---|---|
| | For detecting type A gene cluster | For detecting type B gene cluster | For detecting type C gene cluster-1 | For detecting type C gene cluster-2 |
| 14 | − | − | − | − |
| 15 | − | − | − | − |
| 16 | − | − | − | − |
| 17 | − | − | − | − |
| 18 | − | − | − | − |
| 19 | − | − | − | − |
| 20 | − | − | − | − |
| 21 | − | − | − | − |
| 22 | − | − | − | − |
| 23 | − | − | − | − |
| 24 | − | − | − | − |
| 25 | − | − | − | − |
| 26 | − | − | − | − |
| 27 | − | − | − | − |
| 28 | − | − | − | − |
| 29 | − | − | − | − |
| 30 | − | − | − | − |
| 31 | − | − | − | − |
| 32 | − | − | − | − |
| 33 | − | − | − | − |
| 34 | − | − | − | − |
| 35 | − | − | − | − |
| 36 | − | − | − | − |
| 37 | − | − | − | − |

Test Example 2: Quantitative Properties of Primers Targeting THD-Equol Converting Enzyme Gene (1) Methods A standard curve used for quantitative PCR was generated and used in a manner similar to Test Example 1. Conditions of the quantitative PCR were also similar to those described in Test Example 1, and thus a standard curve of each primer was generated.

(2) Results

With respect to any of the primers, a standard curve having a high linearity within a range of $10^0$ to $10^5$ copy numbers per one PCR reaction was obtained (FIG. 2). Accordingly, it was estimated from the results that at least $10^3$ copy numbers per 1 g of feces was detectable.

Example 2: Detection of THD-Equol Converting Enzyme Gene from Feces-1

(1) Methods (a) Detection of Equol Converting Enzyme Gene from Feces

Testing was performed on 25 healthy adults. The test subjects swallowed a bottle of soy milk drink (about 40 mg of isoflavone was contained per 200 mL) at a dinner on the first day, and provided feces on the second day. DNA was extracted from 20 mg of the collected feces according to a publicly known method (Appl. Environ. Microbiol. 70: 167-73), and the obtained DNA was dissolved using 100 μL of TE buffer.

PCR was performed in a manner similar to Test Example 1 and Test Example 2 using three types of primer sets shown in Table 3 (type C gene cluster-1 was used with respect to type C gene cluster), and detection and quantification of equol converting enzyme genes in the feces were performed.

(b) Measurement of Urinary Equol Concentration

Test subjects of 25 healthy adults swallowed a bottle of soy milk drink (about 40 mg of isoflavone was contained per 200 mL) at a dinner on the first day, and provided first-catch urine on the second day. The collected urine was mixed with 4000 IU/mL of β-glucuronidase (Sigma-Aldrich Japan) solution at a ratio of 1:1 (v/v), subjected to a deconjugation reaction at 37° C. for 24 hours, and then 4 times the amount of methanol was added to the reaction solution. The solution was filtered using Centricut Ultramini (W-MO, KURABO INDUSTRIES LTD.) to obtain a urine sample for LC/MS analysis.

A liquid chromatograph mass spectrometry (LC/MS) was used for measurement of the urine sample. A mass detector ZQ 4000, Alliance HPLC system, and a photodiode array detector (Nihon Waters K.K.) were used as measuring equipment. A separation column used was CadenzaCD-C18 3 μL (inner diameter: 3.0 mm, length: 75 mm, Imtakt), and a mobile phase used was a mixed solution of 0.1% formic acid and acetonitrile. Waters Empower 2 software (Nihon Waters K.K.) was used for quantification of equol.

(2) Results

Any of the three types of the THD-equol converting enzyme genes type A to type C was detected in 15 of 25 test subjects (Table 6). The 15 test subjects, in whom any of the THD-equol converting enzyme genes was detected, was confirmed as equol producers by urinary equol concentration. Accordingly, it was found that the three types of primer sets can be used for detecting the THD-equol converting enzyme genes from feces of a test subject, and determining whether the test subject has equol-producing ability or not.

Example 2 using three types of primer sets shown in Table 3 (both type C gene clusters-1 and -2 were used with respect to type C gene cluster), and detection and quantification of equol converting enzyme genes in the feces were performed. The test subjects swallowed a bottle of soy milk drink (about 40 mg of isoflavone was contained per 200 mL) at a dinner on the first day, and provided first-catch urine and feces on the second day. The urine was used for analysis of equol concentration, and the feces were used for detection and quantification of equol converting enzyme gene numbers.

A urine sample was prepared in a manner similar to Test Example 2.

Urinary equol concentrations were measured in a manner similar to Test Example 1 and Test Example 2.

(2) Results

Feces DNAs of 35 healthy adults were analyzed using each of primers including primers for detecting type A gene cluster, primers for detecting type B gene cluster, and primers for detecting type C gene clusters (type C gene cluster-1 and type C gene cluster-2) shown in Table 3. Any of the three types of the THD-equol converting enzyme genes type A to type C was detected in 13 of 35 test subjects (Table 7). The 13 test subjects, in whom any of the equol converting enzyme genes was detected, was confirmed as THD-equol producers by urinary equol concentration. Also from this testing, it was found that the three types of primer sets (any of type C gene cluster-1 or -2 with respect to type C gene clusters) can be used for detecting THD-equol converting enzyme genes from feces of a test subject, and determining whether the test subject has equol-producing ability or not.

TABLE 6

| No. | Sexuality | Age | Urinary equol concentration (nM) | Gene numbers of THD-equol converting enzyme ($\log_{10}$ copy numbers/g feces) | | |
|---|---|---|---|---|---|---|
| | | | | Type A | Type B | Type C |
| 1 | Male | 31 | ND | ND | ND | ND |
| 2 | Male | 35 | ND | ND | ND | ND |
| 3 | Male | 52 | 19656.4 | 6.8 | ND | ND |
| 4 | Female | 36 | 20427.2 | 8.4 | ND | 5.6 |
| 5 | Male | 46 | 5563.4 | ND | ND | 7.5 |
| 6 | Male | 31 | ND | ND | ND | ND |
| 7 | Female | 28 | 10896.6 | 7.1 | 5.9 | ND |
| 8 | Male | 27 | 3596.8 | ND | ND | 6.4 |
| 9 | Female | 29 | 16725.1 | 7.7 | ND | ND |
| 10 | Male | 27 | 16537.4 | ND | 5.6 | 6.2 |
| 11 | Male | 61 | 18544.2 | 8.4 | 5.0 | 7.2 |
| 12 | Female | 21 | 1610.6 | ND | ND | 5.6 |
| 13 | Female | 35 | ND | ND | ND | ND |
| 14 | Female | 36 | 46428.0 | 8.1 | ND | ND |
| 15 | Male | 52 | 21440.4 | 7.9 | ND | ND |
| 16 | Female | 49 | 14604.8 | ND | ND | 7.6 |
| 17 | Male | 68 | 8552.4 | ND | ND | 5.5 |
| 18 | Male | 28 | 8308 | ND | ND | 6.4 |
| 19 | Female | 24 | 1014.2 | ND | ND | 7.3 |
| 20 | Male | 32 | ND | ND | ND | ND |
| 21 | Female | 39 | ND | ND | ND | ND |
| 22 | Male | 40 | ND | ND | ND | ND |
| 23 | Male | 32 | ND | ND | ND | ND |
| 24 | Male | 29 | ND | ND | ND | ND |
| 25 | Male | 37 | ND | ND | ND | ND |

* A hatched area refers to a test subject (a test subject having equol-producing ability) in whom urinary equol concentration was determined and a THD-equol converting enzyme gene was detected from feces.
ND: Not detected Example 3: Detection of Equol Converting Enzyme Gene from Feces-2

(1) Methods

Testing was performed on 35 healthy adults. PCR was performed in a manner similar to Test Example 1 and Test

TABLE 7

| No. | Sexuality | Age | Urinary equol concentration (nM) | Gene numbers of THD-equol converting enzyme ($\log_{10}$ copy numbers/g feces) | | | |
|---|---|---|---|---|---|---|---|
| | | | | Type A | Type B | Type C-1 | Type C-2 |
| 1 | Male | 55 | 8238 | 6.8 | ND | ND | ND |
| 2 | Female | 30 | ND | ND | ND | ND | ND |
| 3 | Male | 31 | ND | ND | ND | ND | ND |
| 4 | Male | 27 | 8800 | ND | ND | 7.1 | 7.4 |
| 5 | Male | 30 | ND | ND | ND | ND | ND |
| 6 | Male | 33 | ND | ND | ND | ND | ND |
| 7 | Female | 27 | 1321 | 6.7 | ND | 5.2 | 5.8 |
| 8 | Male | 39 | 1227 | ND | ND | 5.7 | 5.6 |
| 9 | Male | 41 | 1256 | ND | ND | 6.5 | 6.8 |
| 10 | Male | 41 | 1499 | ND | ND | 6.3 | 6.7 |
| 11 | Male | 28 | ND | ND | ND | ND | ND |
| 12 | Male | 37 | 370 | ND | ND | 7.1 | 7.6 |
| 13 | Male | 40 | ND | ND | ND | ND | ND |
| 14 | Male | 48 | ND | ND | ND | ND | ND |
| 15 | Male | 59 | 17929 | ND | ND | 6.9 | 7.4 |
| 16 | Male | 34 | ND | ND | ND | ND | ND |
| 17 | Male | 49 | ND | ND | ND | ND | ND |
| 18 | Male | 49 | ND | ND | ND | ND | ND |
| 19 | Male | 42 | ND | ND | ND | ND | ND |
| 20 | Male | 26 | ND | ND | ND | ND | ND |
| 21 | Male | 29 | ND | ND | ND | ND | ND |
| 22 | Female | 25 | ND | ND | ND | ND | ND |
| 23 | Male | 55 | 50986 | 7.8 | 5.1 | ND | ND |
| 24 | Male | 42 | ND | ND | ND | ND | ND |
| 25 | Female | 32 | 8070 | 7.4 | ND | ND | ND |
| 26 | Female | 25 | ND | ND | ND | ND | ND |
| 27 | Male | 52 | ND | ND | ND | ND | ND |
| 28 | Male | 26 | 8193 | ND | 5.7 | ND | ND |
| 29 | Male | 45 | 44213 | 5.6 | ND | 7.6 | 7.7 |
| 30 | Male | 34 | ND | ND | ND | ND | ND |
| 31 | Male | 31 | ND | ND | ND | ND | ND |
| 32 | Male | 38 | ND | ND | ND | ND | ND |
| 33 | Male | 27 | ND | ND | ND | ND | ND |

TABLE 7-continued

| | | | Urinary equol concentra- tion (nM) | Gene numbers of THD-equol converting enzyme (log₁₀ copy numbers/g feces) | | | |
|---|---|---|---|---|---|---|---|
| No. | Sexu- ality | Age | | Type A | Type B | Type C-1 | Type C-2 |
| 34 | Female | 28 | ND | ND | ND | ND | ND |
| 35 | Male | 27 | 19893 | ND | ND | 8.0 | 7.7 |

* A hatched area refers to a test subject (a test subject having equol-producing ability) in whom urinary equol concentration was determined and a THD-equol converting enzyme gene was detected from feces.
ND: Not detected Reference Example: Confirmation of Primers for Detecting Type a Gene Cluster (1) Methods In connection with primers for detecting type A gene cluster of Example 1, such primers (SL-F1 and SL-R1 shown in Table 8) were produced on the basis of sequences of THD-equol converting enzyme genes contained in 2 strains including *Slackia* sp. YIT 11861 and *Slackia isoflavoniconvertens* HE8 (i.e., without consideration of the sequence of THD-equol converting enzyme gene contained in *Slackia* sp. MC6).

PCR was performed on human feces of 25 test subjects described in Example 2 in a manner similar to Example 2 using the thus produced primers (SL-F1 and SL-R1) and primers for detecting type A gene cluster (SL-F2 and SL-R2) shown in Table 3, and detection of THD-equol converting enzyme genes from the feces were performed.

TABLE 8

| Primer name | Sequence (5'-3') |
|---|---|
| SL-F1 | GAAGATGATCCCAATGAGGT (SEQ ID NO: 8) |
| SL-R1 | TGGGAGAGGATGGACCATAC (SEQ ID NO: 9) |

(2) Results

Although a test subject No. 3 shows high urinary equol concentration and has equol-producing ability, a THD-equol converting enzyme gene in feces of the test subject No. 3 was not detected using primers SL-F1 and SL-R1 (Table 9). In the test subject No. 3, the THD-equol converting enzyme gene was detected solely by using primers for detecting type A gene cluster (SL-F2 and SL-R2) of the present invention (Table 6). Accordingly, it is necessary to use SL-F2 and SL-R2 as primers for detecting type A gene cluster.

TABLE 9

| | | | Urinary equol concentration (nM) | Gene numbers of THD-equol converting enzyme (log₁₀ copy numbers/g feces) | |
|---|---|---|---|---|---|
| No. | Sexuality | Age | | SL-F1 and SL-R1 | SL-F2 and SL-R2 |
| 1 | Male | 31 | ND | ND | ND |
| 2 | Male | 35 | ND | ND | ND |
| 3 | Male | 52 | 19656.4 | ND | 6.8 |
| 4 | Female | 36 | 20427.2 | 8.7 | 8.4 |
| 5 | Male | 46 | 5563.4 | ND | ND |
| 6 | Male | 31 | ND | ND | ND |
| 7 | Female | 28 | 10896.6 | 7.0 | 7.1 |
| 8 | Male | 27 | 3596.8 | ND | ND |
| 9 | Female | 29 | 16725.1 | 7.7 | 7.7 |
| 10 | Male | 27 | 16537.4 | ND | ND |
| 11 | Male | 61 | 18544.2 | 8.5 | 8.4 |
| 12 | Female | 21 | 1610.6 | ND | ND |
| 13 | Female | 35 | ND | ND | ND |
| 14 | Female | 36 | 46428.0 | 8.8 | 8.1 |
| 15 | Male | 52 | 21440.4 | 8.1 | 7.9 |
| 16 | Female | 49 | 14604.8 | ND | ND |
| 17 | Male | 68 | 8552.4 | ND | ND |
| 18 | Male | 28 | 8308 | ND | ND |
| 19 | Female | 24 | 1014.2 | ND | ND |
| 20 | Male | 32 | ND | ND | ND |
| 21 | Female | 39 | ND | ND | ND |
| 22 | Male | 40 | ND | ND | ND |
| 23 | Male | 32 | ND | ND | ND |
| 24 | Male | 29 | ND | ND | ND |
| 25 | Male | 37 | ND | ND | ND |

* A hatched area refers to a test subject in whom the gene was detected using SL-F2 and SL-R2 and was not detected using SL-F1 and SL-R1.

The invention claimed is:

1. A method for measuring equol-producing ability of a test subject, the method comprising detecting a THD-equol converting enzyme gene derived from enteric bacteria of the test subject using the following three primer sets a) to c):
   a) a primer pair comprising a first oligonucleotide selected from the group consisting of SEQ ID NO:1 and a sequence that is fully complementary thereto; and a second oligonucleotide selected from the group consisting of SEQ ID NO:2 and a sequence that is fully complementary thereto;
   b) a primer pair comprising a first oligonucleotide selected from the group consisting of SEQ ID NO:3 and a sequence that is fully complementary thereto; and a second oligonucleotide selected from the group consisting of SEQ ID NO:4 and a sequence that is fully complementary thereto; and
   c) a primer pair comprising a first oligonucleotide selected from the group consisting of SEQ ID NO:5 and a sequence that is fully complementary thereto; and a second oligonucleotide selected from the group consisting of SEQ ID NO:6, a sequence that is fully, complementary to SEQ ID NO:6, SEQ ID NO:7, and a sequence that is fully complementary to SEQ ID NO:7.

2. The method according to claim 1, wherein the THD-equol converting enzyme gene is detected using feces derived from the test subject.

* * * * *

SEQUENCE LISTING

<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 1
cccgcgcatt tgtggagaac t        21

<210> SEQ ID NO 2
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 2
cgttccgata tcgccgaggt tt                                        22

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
cgctgccttc gagtcctcta                                           20

<210> SEQ ID NO 4
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 4
ggtggaggtg aagatgtcg                                            19

<210> SEQ ID NO 5
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 5
cgttcgatac tgagtacgac ctg                                       23

<210> SEQ ID NO 6
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 6
atccttgagg aaatcgatgg ta                                        22

<210> SEQ ID NO 7
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 7
agtttgcgcg atagtggctg ta                                        22

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
gaagatgatc ccaatgaggt                                           20

<210> SEQ ID NO 9
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 9
tgggagagga tggaccatac                                                   20
```